United States Patent [19]

Garvey et al.

[11] Patent Number: 4,725,628
[45] Date of Patent: Feb. 16, 1988

[54] PROCESS OF MAKING A CROSSLINKED SUPERABSORBENT POLYURETHANE FOAM

[75] Inventors: Chad E. Garvey, Ball Ground; Jose F. Pazos, Roswell; Gerard J. F. Ring, Woodstock, all of Ga.

[73] Assignee: Kimberly-Clark Corporation, Neenah, Wis.

[21] Appl. No.: 888,545

[22] Filed: Jul. 18, 1986

[51] Int. Cl.⁴ .................... C08L 75/00; C08G 18/10; C08G 18/67
[52] U.S. Cl. .................................. 521/137; 521/905; 528/66; 528/75
[58] Field of Search ................. 521/137, 905; 528/66, 528/75

[56] References Cited

U.S. PATENT DOCUMENTS

| | | | |
|---|---|---|---|
| 2,920,983 | 1/1960 | Bugosh | 521/905 |
| 3,382,090 | 5/1968 | Meisel et al. | 521/905 |
| 3,860,537 | 1/1975 | Graham et al. | 521/137 |
| 4,359,558 | 11/1982 | Gould et al. | 521/905 |

Primary Examiner—Harold D. Anderson
Assistant Examiner—Dennis R. Daley
Attorney, Agent, or Firm—William E. Maycock

[57] ABSTRACT

A superabsorbent polyurethane foam which contains a plurality of polycarbonyl moieties covalently attached to the polyurethane through at least one urethane, thiourethane, or urea linkage. The carbonyl portions of such polycarbonyl moieties can be carbamoyl, substituted carbamoyl, or carboxy or the alkali metal or ammonium salts thereof. The foam can be prepared by mixing an isocyanate-terminated prepolymer with a first compound having at least one isocyanate-reactive group and at least one carbon-carbon double bond, allowing the mixture to react, and then mixing with the resulting product an aqueous solution of a carboxylate-containing second compound having at least one carbon-carbon double bond. A thermally activated free radical initiator is present in the final reaction mixture.

Preferably, the polyurethane is derived from an isocyanate-terminated poly(oxyalkylene) polyol having an isocyanate functionality greater than two and the polycarbonyl moieties are derived from second compounds which typically are acrylate or methacrylate salts, i.e., alkali metal or ammonium salts of acrylic or methacrylic acid. The first compound usually is the 2-hydroxyethyl ester of acrylic or methacrylic acid.

Such superabsorbent polyurethane foam is useful in the manufacture of absorbent articles, especially disposable absorbent articles such as diapers, sanitary napkins, bedpads, incontinent pads, and the like.

7 Claims, No Drawings

PROCESS OF MAKING A CROSSLINKED SUPERABSORBENT POLYURETHANE FOAM

CROSS-REFERENCES TO RELATED APPLICATIONS

A superabsorbent polyurethane foam based on an interpenetrating polymer network of a crosslinked polyurethane and a crosslinked addition polymer containing a plurality of carbamoyl, substituted carbamoyl, or carboxy groups or the alkali metal or ammonium salts thereof, is described in application Ser. No. 888,301, entitled SUPERABSORBENT POLYURETHANE FOAMS, filed of even date in the names of Chad E. Garvey and Jose F. Pazos and assigned to the assignee of the present application.

A superabsorbent polyurethane foam based on a quasi-interpenetrating polymer network of a crosslinked polyurethane and a substantially linear addition polymer containing a plurality of carbamoyl, substituted carbamoyl, or carboxy groups or the alkali metal or ammonium salts thereof, is described in application Ser. No. 888,548, entitled SUPERABSORBENT POLYURETHANE FOAMS, filed of even date in the name of Chad E. Garvey and assigned to the assignee of the present application.

BACKGROUND OF THE INVENTION

The present invention relates to polyurethane foams. More particularly, the present invention relates to polyurethane foams having greatly enhanced absorbent capabilities; i.e., superabsorbent polyurethane foams.

Polyurethane foams are, of course, well known to those having ordinary skill in the art. Indeed, a voluminous body of literature has accumulated over the years as researchers explored combinations of starting materials and correlated starting materials with foam properties. Moreover, numerous efforts have been made to either modify the physical properties of polyurethane foams or to prepare specialized polyurethane foams having unique properties. A particularly sought-after property is increased water absorbency. Polymers having this property often are referred to as hydrogels or superabsorbents.

The nature and utility of superabsorbents are illustrated by U.S. Pat. No. 4,449,977, although it will be appreciated by those having ordinary skill in the art that numerous other references also could be cited. According to this reference, an apparently desirable feature of a superabsorbent is the presence of acrylate or methacrylate groups which can be salts, amides, esters, or the free acids.

As a practical matter, many hydrogels are based on acrylate and methacrylate polymers and copolymers. See, by way of example only, U.S. Pat. Nos. 2,976,576, 3,220,960, 3,993,616, 4,154,898, 4,167,464, 4,192,727, 4,192,827, and 4,529,739. The last-cited patent is of particular interest since the disclosed water-absorbent polymers are foamed. Other hydrogels are based on starch or a modified starch, as shown by U.S. Pat. Nos. 4,069,177, 4,076,663, 4,115,332, and 4,117,222. Still other hydrogels are based om poly(oxyalkylene)-glycols; see, e.g., U.S. Pat. No. 3,783,872. Hydrogels prepared from hydrolyzed crosslinked polyacrylamides and crosslinked sulfonated polystyrenes are described in U.S. Pat. No. 4,235,237. Finally, polymers based on maleic anhydride (or similar compounds) have been described in U.S. Pat. Nos. 2,988,539, 3,393,168, 3,514,419, 3,557,067, and 4,401,793. U.S. Pat. No. 3,900,378 is of interest since it describes hydrogels from radiation crosslinked blends of hydrophilic polymers and fillers, many of the polymers being those described in the foregoing patents. However, such materials are not necessarily well suited for the uses described in U.S. Pat. No. 4,449,977, supra.

Polyurethane hydrogels are, of course, known and frequently are based on the reaction of a poly(oxyalkylene)polyol with a diisocyanate. However, relatively few of such hydrogels contain acrylate or methacrylate moieties, or even carboxylate groups. Examples of carboxylate-containing polyurethanes and polyurethane hydrogels are noted below.

U.S. Pat. No. 3,928,299 describes the reaction of a hydroxy group-containing polymer with an unsaturated isocyanate. Suitable hydroxy group-containing polymers can be obtained by the polymerization of hydroxyalkyl esters of acrylic acid or alpha-alkyl-substituted acrylic acids or by the copolymerization of these compounds with other vinyl or vinylidene compounds. Suitable hydroxyalkyl esters are the monoesters of the foregoing acids with ethylene glycol, propylene glycol, propane-1,3-diol, butanediol, diethylene glycol, and higher polyethylene glycols. Such polymers also can be polyesters of polybasic aliphatic or aromatic carboxylic acids with polyhydric alcohols, polyurethanes which contain hydroxy groups, or epoxy resins which contain hydroxy groups. The resulting polymers are crosslinkable by vinyl polymerization and are useful for the preparation of coatings and molded products. Foams, especially polyurethane foams, are not mentioned. See also U.S. Pat. No. 4,210,173.

Disclosures similar to that of the above patent are found in U.S. Pat. Nos. 3,871,908, 3,856,830, 3,954,714, and 4,082,710.

U.S. Pat. No. 4,131,602 describes radiation-curable acrylated polyurethane coating compositions. The compositions are prepared by reacting an isocyanate-terminated urethane intermediate with an amount of a hydroxyalkyl, hydroxycycloalkyl, or hydroxyaryl ester of acrylic acid or methacrylic acid which is sufficient to react with at least 80 percent of the isocyanate groups of the urethane intermediate. The urethane intermediate is the reaction product of an organic diisocyanate, an organic triol or tetraol which is either a polyester or a polyether, and an organic diol which is either a polyester or a polyether. The diisocyanate is used in an equivalent excess to the other two components. In addition, when the triol or tetraol is a polyester, the diol must be a polyether, and when the triol or tetraol is a polyether, the diol must be a polyester.

U.S. Pat. No. 4,153,778 describes acrylyl-capped urethane oligomers which readily cure by thermal or radiation means and are useful as coatings, binders, and adhesives. The oligomers are the reaction products of a poly(oxytetramethylene)diol or a polycaprolactone polyol, an organic diisocyanate, a di- or trimethylol carboxylic acid, and an acrylyl compound.

Polyester urethane-containing molding compositions are described in U.S. Pat. No. 4,287,116. Briefly, an ethylenically unsaturated monomer solution having dissolved therein a polyester urethane resin and an organic polyol polyurethane precursor is gelled by the addition of a polyisocyanate polyurethane precursor. The gelled mixture then is molded and cured by copolymerization of the ethylenically unsaturated monomer and the resin. The resin typically is a condensation product of a dihydroxy-terminated poly(oxyalkylene)-bisphenol A maleate or fumarate and a polyisocyanate which is further reacted with a hydroxy-terminated ester of acrylic or methacrylic acid. The polyol precursor is a saturated aliphatic polyol or alkoxylated derivative thereof. The ethylenically unsaturated monomer can be, by way of illustration, styrene, vinyltoluene, divinylbenzene, esters of acrylic or methacrylic acid, vinyl acetate, divinyl ether, and the like. Finally, the polyisocyanate precursor is an aliphatic, cycloaliphatic, or aromatic compound having at least two isocyanate groups.

U.S. Pat. No. 4,480,079 discloses molded plastic products which are produced by the in-mold copolymerization of methyl methacrylate with a polyurethane acrylate or methacrylate. The latter material is derived from a hydroxyalkyl acrylate or methacrylate by reaction of the hydroxy groups thereof with the isocyanate groups of either a polyisocyanate free of urethane groups and having an isocyanate functionality greater than two or a urethane polyisocyanate having an isocyanate functionality greater than two and derived from a polyisocyanate by reaction thereof with the hydroxy groups of an aliphatic alcohol having up to three hydroxy groups.

A series of ten patents relates to polyurethane polyene or diacrylate polymers. These ten patents, discussed briefly below, appear to relate to interpenetrating polymer networks, although such terminology does not appear to have been applied to the polymer compositions described by these references. For general discussions of interpenetrating polymer networks, see, by way of example only, D. Klempner et al., *J. Elastoplastics,* 5, 196 (1973); A. A. Donatelli et al., *Macromolecules,* 9, 671 and 676 (1976); L. H. Sperling et al., *Macromolecules,* 9, 743 (1976); L. H. Sperling, *J. Polymer Science,* 12, 141 (1977); and D. L. Siegfried et al., *J. Polymer Science,* 16, 583 (1978).

U.S. Pat. No. 4,359,558 discloses hydrophilic polyurethane diacrylate compositions. The compositions, which form hydrogels upon immersion in water, are prepared by reacting a diacrylate in the presence of a hydrophilic polyurethane. A free radical initiator may be present. The polyurethane typically is the reaction product of one or more diols having a number average molecular weight in the range of from about 200 to about 20,000, selected from the group consisting of ethylene glycol and long chain poly(oxyalkylene)diols, with a urethane precursor selected from the group consisting of organic polyisocyanates and nitrile carbonates in the presence of an organic tin catalyst. Optionally, a polyfunctional lactone also may be present in amounts of from 0.1 to 30 percent by weight, based on the weight of the total reaction mixture. The long chain diols typically are the condensation products of either ethylene oxide or propylene oxide. The diacrylate may be prepared by reacting acrylic acid chloride (propenoyl chloride) or methacrylic acid chloride (2-methylpropenoyl chloride) with a glycol such as ethylene glycol or a condensation product of either ethylene oxide or propylene oxide. The two components are dissolved in a suitable solvent, cast as a film, and cured by heat or ultraviolet radiation. See also U.S. Pat. Nos. 4,408,023, 4,424,305, 4,439,583, 4,439,584, and 4,439,585.

Hydrophilic polyurethane acrylate compositions are disclosed in U.K. Patent Application GB No. 2,150,938A. The disclosure is similar to that of U.S. Pat. No. 4,359,558 et al., except that the diacrylate is replaced with an acrylate which is the monoacrylic or monomethacrylic ester of an alcohol having less than 13 carbon atoms. The preferred acrylates are stated to be hydroxyethyl acrylate, methyl methacrylate, and methyl acrylate. The polyurethane and acrylate components are dissolved in a solvent, optionally in the presence of a free radical initiator, cast as a film, and cured thermally or by ultraviolet radiation. Shaped articles can be made by removing the solvent under reduced pressure, molding the residual mixture, and curing the molded article thermally.

Hydrophilic polyurethane polyene compositions are disclosed in U.S. Pat. No. 4,454,309. The compositions are prepared by reacting a polyene in the presence of a hydrophilic polyurethane. The polyene is either a polyallyl ester of a polybasic acid or a polyacrylic or polymethacrylic ester of a polyhydric alcohol. The polyurethane is that described in U.S. Pat. No. 4,359,558. As with the compositions of such earlier patent, the components are dissolved in a suitable solvent, cast as a film, and cured with heat or ultraviolet radiation. Alternatively, the solvent may be removed under reduced pressure and the residual mixture molded and cured thermally. See also U.S. Pat. Nos. 4,490,423 and 4,496,535.

In each of the foregoing references, the unsaturated monomers are polymerized in the presence of an existing polymer, i.e., a polyurethane. A similar approach is disclosed in U.S. Pat. No. 4,551,486. According to the patent, hardenable dental compositions are prepared by polymerizing crosslinking oligomers in the presence of a crosslinked polymer and one or more of a filler, an initiator, and a monofunctional monomer. The crosslinked polymer can be a polyurethane, although the preferred polymers are derived from aliphatic, cycloaliphatic, phenyl, and substituted phenyl esters of acrylic acid and homologs thereof. The crosslinking agents which are useful in the preparation of the crosslinked polymer can be selected from a wide variety of polyfunctional materials. The preferred functionality apparently is an ethylenic function, presumably because the preferred polymers are prepared by the addition polymerization of unsaturated monomers. The crosslinking oligomers also tend to be polyunsaturated compounds, such as acrylic and lower alkyl acrylic acid diesters, acrylic and lower alkyl acrylic acid esters of alcohols having a second reactive function, urethane diacrylates and dimethacrylates, polyvinyl compounds, divinyl aromatic compounds, and the like. Preferred compounds include allyl acrylate allyl methacrylate, vinyl acrylate, vinyl methacrylate, dimethallyl fumarate, N-allyl-acrylamide, crotyl acrylate, allyl crotonate, allyl cinnamate, diallyl maleate, acrylate and methacrylate esters of polyols, and the like.

The reverse approach is described in European Patent Application No. 85105252.2, published at 0,163,150. In general, a polyurethane foam is prepared in the presence of a polyelectrolyte polymer. Preferably, the polyurethane is prepared from an isocyanate-terminated poly(oxyalkylene)polyol, such as the HYPOL® precursor sold by W. R. Grace & Co. The crosslinking agents are selected to react with the carboxylic acid groups of the polyelectrolyte polymer and include polyhaloalkanols, haloepoxyalkenes, polyglycidyl ethers, defined di- and triaziridines, and the like. The polyelectrolyte polymers tend to be polymers or copolymers of acrylic and methacrylic acid with such monomers as acrylates, methacrylates, acrylamide, olefins, vinyl aromatic compounds, styrenesulfonic acid, vinyl ethers, vinyl acetate, vinyl alcohol, maleic acid, fumaric acid, and the like. The examples used a polyacrylic acid which had been treated with sodium hydroxide.

It perhaps should be noted at this point that interpenetrating polymer networks ideally do not include any grafting of the first polymer to the second, although, as noted by Donatelli et al., some grafting may take place accidentally. Because of the selection of polymer types described in the foregoing interpenetrating polymer network references, little, if any, grafting should have taken place.

Acrylic monomers containing carbamate (urethane) functionality are described in U.S. Pat. Nos. 3,297,745, 3,425,988, 4,129,667, and 4,279,833. An acrylic monomer containing isocyanate functionality, isocyanatoethyl methacrylate, is described in Adhesives Age, October, 1984. The article summarizes three areas in which isocyanatoethyl methacrylate has been used: (1) applications where the methacrylate group is polymerized first, leaving the isocyanate group for a later reaction, (2) applications where the isocyanate group is reacted with a polyfunctional material first, leaving the vinyl group for a later reaction, and (3) applications where the isocyanate group is reacted with a monofunctional reagent first to make a new monomer which can be polymerized later.

Because a significant amount of the voluminous polyurethane foam literature relates to the use as a starting material of what may be termed polyether polyols, polyglycol ethers, or poly(oxyalkylene)polyols and such starting material has acquired a singularly important status in the polyurethane art, a discussion of representative references relating thereto is deemed necessary for the sake of completeness.

One of the earliest references describing such materials is U.S. Pat. No. 2,948,691. According to this patent, polyglycol ethers having a molecular weight of at least 500 and at least two terminal hydroxy groups can be reacted with mono- or polyfunctional isocyanates to give products which may be used for producing plasticizers, lubricants, plastics, spongy materials, gel formers, thickening agents, and the like. The patent describes the preparation of hydrogels and foams.

Subsequent studies with these poly(oxyalkylene)polyols demonstrated a high suitability for the preparation of hydrogels and foams having particular properties, as illustrated by the references described below.

U.S. Pat. No. 3,861,993 describes a composite foam scouring pad, one component of which is a hydrophilic foam composition prepared by reacting an isocyanate-capped poly(oxyethylene)polyol having an isocyanate functionality of at least two with an aqueous solution containing a blowing agent such as a polyisocyanate, a nonionic surfactant, and, when the isocyanate-capped poly(oxyethylene)polyol isocyanate functionality is about two, a crosslinking agent. The ratio of moles of water to moles of isocyanate functionality in the polyol can range from about 6.5 to about 390. The same hydrophilic foam is employed to prepare a laminated fabric as described in U.S. Pat. No. 3,874,964 and a horticultural foam structure as described in U.S. Pat. No. 3,889,417. The reticulated crosslinked polyurethane foam described in U.S. Pat. No. 3,890,254 appears to differ from that described above in that particular types of surfactants are required and the isocyanate-capped poly(oxyethylene)polyol is derived from a poly(oxyethylene)polyol having a weight average molecular weight of from about 200 to about 20,000 and a hydroxy group functionality of from about 2 to about 8. See also U.S. Pat. No. 4,160,076.

Compressed foams which are restored to their original volume in the presence of water or heat are disclosed in U.S. Pat. No. 3,903,232; see also U.S. Pat. No. 3,854,535. The foams are similar to those described in U.S. Pat. No. 3,861,993. Briefly, a mixture of from 0 to about 97 percent by weight of an isocyanate-capped hydrophilic poly(oxyethylene)polyol having an isocyanate functionality of two and an isocyanate-capped poly(oxyethylene)polyol having an isocyanate functionality of from about 3 to about 8 and a weight average molecular weight of from about 200 to about 1,500 (20,000 according to claim 1) is reacted with water, optionally in the presence of a crosslinking agent. The ratio of moles of water to moles of isocyanate groups can range from about 6.5 to about 390. See also U.S. Pat. Nos. 4,156,592 and 4,292,412 which disclose the use of such foams in the preparation of expandable fabric softener-containing articles and hydrophilic fabric softener foam compositions, respectively. Similar foams are disclosed in U.S. Pat. Nos. 4,110,508 and 4,137,200 in which the poly(oxyethylene)polyol moiety of the isocyanate-capped polyol has a weight average molecular weight of from about 200 to about 20,000. See also U.S. Pat. Nos. 4,201,846, 4,258,137, and 4,309,509 which describe the incorporation into the foam of U.S. Pat. No. 4,137,200 hydrophilic fibers prepared from vinyl alcohol homopolymers and copolymers, an epoxy resin, and an odorant, respectively. In addition, U.S. Pat. No. 4,127,516 describes the inclusion of a polyurea in the reaction mixture which yields the foams of U.S. Pat. No. 4,110,508. The polyurea is prepared by, for example, the reaction between a linear poly(oxyethylene) polyol which has been capped with a polyisocyanate and a polyamine in an organic solvent.

U.S. Pat. No. 3,904,557 describes a method for producing a multicolored polyurethane sponge. A poly(oxyethylene)polyol having a weight average molecular weight of from about 200 to about 20,000 and a hydroxy functionality of from about 2 to about 8 is capped with a polyisocyanate. At least two distinctly different coloring agents are added to at least two different portions of isocyanate-capped polyol or water. The colored portions then are reacted with separate portions of water or isocyanate-capped polyol, respectively, to form separate colored foaming masses which then are mixed together under laminar flow conditions to yield a multicolored variegated polyurethane foam.

A polyurethane hydrogel is described in U.S. Pat. No. 4,118,354. The hydrogel is produced by dispersing into an aqueous liquid phase a product obtained by the reaction of a polyisocyanate having at least two isocyanate groups with a polyether. The polyether results from the polycondensation of at least two alkylene oxides with a polyalcohol having at least two hydroxy groups and has an average molecular weight per hydroxy group of from 1,000 to 4,000. Preferably, 75 to 85 percent of the alkylene oxides is ethylene oxide. The resulting hydrogen is stated to have a greater water content and to be highly elastic and highly stable, even in the presence of a corrosive electrolyte solution.

Urethane foams having low resiliency are described in U.S. Pat. No. 4,158,087. The foams are obtained by reacting a poly(oxyalkylene) urethane prepolymer containing at least 40 mole percent of oxyethylene units in the oxyalkylene portion of the prepolymer, water, and from about 40 to about 150 parts by weight on a solids basis per 100 parts by weight of the prepolymer of a synthetic polymer latex. The prepolymer is an isocyanate-capped poly(oxyethylene) polyol of the type described in U.S. Pat. Nos. 3,903,232 et seq.

U.S. Pat. No. 4,181,770 describes the preparation of a hydrophilic foam from an isocyanate-terminated branched polyethylene polyol, an isocyanate-terminated polyester prepolymer, a minor amount of a 4,4'-diphenylmethanediisocyanate/polycarbodiimide liquid condensation product which has 30 percent free isocyanate groups, and water. The foam is stated to have improved firmness and scuff resistance properties.

Isocyanate-capped urethane-containing prepolymers prepared from polyols obtained from an epihalohydrin are described in U.S. Pat. Nos. 4,273,913 and 4,297,482. The polyol can be, for example, a polyalkylene glycol composed of the same or different oxyalkylene units or a mixture of different polyalkylene glycols.

U.S. Pat. Nos. 4,314,034, 4,365,025, 4,377,645, 4,384,050, and 4,384,051 describe variations of a general concept which involves mixing a resin phase and an aqueous phase. The resin phase comprises an isocyanate-capped poly(oxyalkylene)glycol of the type described in U.S. Pat. Nos. 3,903,232 et seq. and diphenylmethane diisocyanate and/or polymeric forms or isocyanate-containing derivatives thereof.

Finally, mention should be made of U.S. Pat. Nos. 3,412,054 and 4,156,066. The first patent describes water-dilutable polyurethanes which are useful as surface coatings and printing inks. Such polyurethanes contain carboxylic acid groups which can be neutralized with ammonia or an amine. The carboxylic acid groups are provided by incorporating into the polyurethane a 2,2-bis(hydroxymethyl)-substituted carboxylic acid. Examples of suitable acids include 2,2-bis(hydroxymethyl)acetic acid, 2,2,2-tris(hydroxymethyl)acetic acid, 2,2-bis(hydroxymethyl)propionic acid, 2,2-bis(hydroxymethyl)butyric acid, 2,2-bis(hydroxymethyl)pentanoic acid, and the like. The polyurethanes are prepared by known techniques, such as by adding organic diisocyanate to a mixture of a suitable carboxylic acid and a polyol polyurethane precursor.

The second patent, U.S. Pat. No. 4,156,066, discloses polyurethanes characterized by lactone groups and hydroxy groups in the polymer backbone. The polyurethanes are prepared by reacting an organic polyisocyanate with a poly(oxyalkylene) polyol and a polyfunctional lactone having excess hydroxy groups. The free hydroxy groups which are present in the formed polyurethane are available for crosslinking the polymer. The lactone groups can be hydrolyzed to form free carboxylic acid groups or carboxylate groups.

In addition to efforts directed at altering the nature of the polyurethane per se, as noted at length above, other efforts have been directed at either incorporating into the polyurethane foam a material which will give the desired property or preparing a foam of an entirely different type. Both of these approaches are illustrated by the references which are summarized in the paragraphs which follow.

U.S. Pat. No. 3,900,030 describes a polyurethane foam of approximately the same type as those disclosed in U.S. Pat. No. 3,903,232 et. seq. which has dispersed throughout the foam a particulate, water-swellable polymer containing a plurality of hydrophilic groups such as carboxy, carboxamide, sulfonate salt, or hydroxy groups. The particulate polymer is included to increase the water absorbency of the foam.

According to U.S. Pat. No. 4,377,160, a sheet or strip of a polyurethane foam is dipped first into a polyvinyl alcohol solution and then into a reactive gelling agent solution in order to gel the polyvinyl alcohol in the foam. The resulting gel-impregnated foam is useful as a cooling compression bandage.

Finally, U.S. Pat. No. 4,098,728 discloses foams prepared by the copolymerization of polyvinyl alcohol and formaldehyde. The foams are stated to be useful as surgical sponges. The patent notes deficiencies with polyurethane sponges which are related to the generally hydrophobic nature of polyurethanes. The patent also states that fast wicking and high liquid holding capacity are desirable qualities of surgical sponges, qualities which apparently are lacking in polyurethane sponges.

It is evident that the polyurethane foams of the prior art, while certainly admirable for many applications, suffer from various disadvantages for a number of uses. Many of these disadvantages are associated with the generally hydrophobic nature of polyurethanes. Consequently, in spite of the prior art efforts to prepare superabsorbent foams, there still is a need for improvements with regard to such materials.

SUMMARY OF THE INVENTION

Consequently, it is an object of the present invention to provide superabsorbent polyurethane foams.

It also is an object of the present invention to provide superabsorbent polyurethane foams which contain a plurality of polycarbonyl moieties covalently attached to the polyurethane through at least one urethane, thiourethane, or urea linkage.

It also is an object of the present invention to provide superabsorbent polyurethane foams which are prepared from isocyanate-terminated poly(oxyalkylene) polyols.

It is a further object of the present invention to provide superabsorbent polyurethane foams prepared from isocyanate-terminated poly(oxyalkylene) polyols, which foams contain a plurality of polycarbonyl moieties covalently attached to the polyurethane through at least one urethane, thiourethane, or urea linkage.

Still another object of the present invention is to provide superabsorbent polyurethane foams prepared from isocyanate-terminated poly(oxyalkylene) polyols, which foams contain a plurality of polycarbonyl moieties covalently attached to the polyurethane through at least one urethane, thiourethane, or urea linkage, such moieties being derived from acrylates or methacrylates.

These and other objects will be readily apparent to those having ordinary skill in the art from a reading of the specification and claims which follow.

Accordingly, the present invention provides a superabsorbent polyurethane foam which contains a plurality of polycarbonyl moieties covalently attached to the polyurethane through at least one urethane, thiourethane, or urea linkage, said polycarbonyl moieties comprising from about 5 to about 100 carbonyl-containing repeating units which may be the same or different, the carbonyl portions being independently selected from the group consisting of carbamoyl, substituted carbamoyl, and carboxy and alkali metal and ammonium salts thereof.

In preferred embodiments, the polyurethane is derived from an isocyanate-terminated poly(oxyalkylene) polyol having an isocyanate functionality greater than two and the polycarbonyl moieties are derived from acrylate or methacryate salts, i.e., alkali metal or ammonium salts of acrylic or methacrylic acid.

The present invention also provides a method of preparing a superabsorbent polyurethane foam which comprises the steps of:

A. mixing an isocyanate-terminated polyurethane prepolymer having an isocyanate functionality greater than two with at least one first compound having at least one isocyanate-reactive group and at least one carbon-carbon double bond, the amount of said first compound being insufficient to reduce the isocyanate functionality of the prepolymer to a value equal to or less than two;

B. allowing the mixture obtained in Step A to substantially completely react; and C. mixing the reaction product from Step B with an aqueous solution of at least one carbonyl-containing second compound having at least one carbon-carbon double bond capable of undergoing addition polymerization with said first compound and with itself under the conditions of the polyurethane foam formation, the carbonyl group of said second compound being selected from the group consisting of carbamoyl, substituted carbamoyl, and carboxy and the alkali metal and ammonium salts thereof;

in which at least one thermally activated free radical initiator has been dissolved in either the reaction product from Step B or said aqueous solution, said carbon-carbon double bond of said first compound is capable of undergoing addition polymerization with said second compound under the conditions of the polyurethane foam formation; and the proportions of said first and second compounds are selected to impart superabsorbent properties to the resulting polyurethane foam.

If desired, the reaction product from Step B, or modified prepolymer, can be reacted with one or more third compounds having at least two carbon-carbon double bonds capable of both homopolymerization with other third compound molecules and copolymerization with the first compound(s) present in the modified prepolymer. Such reaction is carried out in the presence of a free radical initiator.

In preferred embodiments, said isocyanate-reactive group of said first compound is selected from the group consisting of hydroxy, mercapto, and amino groups. In other preferred embodiments, said first compound contains a carbonyl group selected from the group consisting of carbamoyl, substituted carbamoyl, and carboxy and esters thereof. In still other preferred embodiments, said first compound is selected from the group consisting of hydroxyethyl acrylate and hydroxyethyl methacrylate and said second compound is selected from the group consisting of acrylamide, methacrylamide, potassium acrylate, and potassium methacrylate. In yet other preferred embodiments, the prepolymer is an isocyanate-terminated poly(oxyalkylene) polyol.

DETAILED DESCRIPTION OF THE INVENTION

Since the term "carboxylate" includes both esters and salts of carboxylic acids, these two classes of compounds will be distinguished throughout this specification by using the terms "carboxylate esters" and "carboxylate salts," respectively, or specific equivalents thereof, unless the class is clear from the name of the compound(s).

As used herein, the term "ammonium" is used throughout the specification and claims to mean any quaternary ammonium ion derived from ammonia or primary, secondary, or tertiary amines, the choice of such amines being limited only to the extent that any given amine significantly adversely affects foam properties.

For convenience, the term "precursor" will be used herein to mean a polyfunctional polyurethane precursor which is reacted with a polyisocyanate to give an isocyanate-terminated material, whereas the term "prepolymer" will refer to the isocyanate-terminated material. The term "modified prepolymer" will be used herein to refer to the reaction product of prepolymer with at least one first compound as described more fully hereinafter. Furthermore, as will be made clear later, each term is intended to include both a single compound or material and a mixture of two or more compounds or materials.

The phrases "at least one first compound," "at least one second compound," and the like are intended to include the use of a single compound or a mixture of two or more compounds. For convenience, however, the use hereinafter of such terms as "first compound," "second compound," and the like shall be read as encompassing both single compounds and mixtures of two or more compounds.

The nature of the polyurethane is not known to be critical. Thus, the polyurethane can contain other moieties, such as polyesters, polyethers, and the like. However, the polyurethane must be crosslinked, as will be made more clear hereinafter, in order to assure foam integrity. Because of the wide variety of polyurethanes which can be prepared within the spirit and scope of the present invention, it is not practical to define precise ranges for the degree of crosslinking which will result in suitable foams. However, one having ordinary skill in the art can readily prepare foams coming within the scope of the present invention, without the need for undue experimentation, by following the guidelines contained herein.

Stated differently, the precursor can be any of the precursor known to those having ordinary skill in the art for the preparation of polyurethane foams. Because the foam must be crosslinked, the precursor should have at least two isocyanate-reactive groups per molecule (referred to hereinafter as precursor isocyanate-reactive functionality, or PICRF), thereby permitting crosslinking by either of two methods which will be described briefly hereinafter. The isocyanate-reactive groups can be the same or different and can be any of the groups known to be reactive with an isocyanate. Such groups include primary aliphatic amines, secondary aliphatic amines, primary aromatic amines, secondary aromatic amines, hydrazines, amides, ureas, urethanes, imides, amidines, nitramines, diazoamino compounds, phenylhydrazones, aminooximes, sulfimides, acylureas, thioureas, isothioureas, primary alcohols, secondary alcohols, phenols, carboxylic acids, malonic esters, nitroalkanes, acetoacetic esters, primary mercaptans, secondary mercaptans, thiophenols, and the like. For a review of groups which are reactive with isocyanates, see J. H. Saunders and K. C. Frisch, "Polyurethanes: Chemistry and Technology. Part I. Chemistry," Vol. XVI, Part I, Interscience Publishers, New York, 1962, pp. 63–128.

The preferred isocyanate-reactive groups are primary and secondary alcohols, primary and secondary amines, and primary and secondary mercaptans. The more preferred groups are the primary alcohols and amines, with the primary alcohols being most preferred.

As a practical matter, polyurethane foams prepared from a poly(oxyalkylene) polyol are preferred, largely because of the water miscibility and ready commercial availability of such polyols and the generally acceptable properties of the resulting foams. Especially useful are the isocyanate-terminated polyurethane prepolymers which are based on such polyols, such as the HY-POL ® prepolymers available from W. R. Grace & Co., Organic Chemicals Division, Lexington, Mass.

As used herein, the terms "poly(oxyalkylene) glycol" and "poly(oxyalkylene) polyol" are intended to be synonymous and to include any poly(oxyalkylene) condensation product containing at least two hydroxy groups. Moreover, such materials may be considered to be derived from one or more alkylene oxides. Thus, the oxyalkylene moiety can be all of one type or a mixture of two or more types. A mixture may be either random or block. In addition, such materials can contain other moieties, such as polyesters, polyamides, and the like, as already indicated.

In general terms, the superabsorbent polyurethane foams of the present invention are prepared in accordance with the following flow diagram:

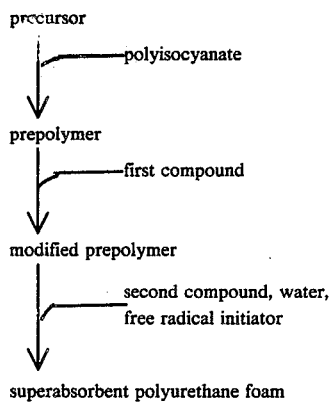

Because the preparation of prepolymers is well known in the art and prepolymers are commercially available, the reaction by which the prepolymers are formed is not deemed to form a part of the method of the present invention. However, since the polyurethane foam must be crosslinked and the preparation of modified prepolymer typically results in a net decrease in the number of available isocyanate groups which can be utilized in the next and final step, some discussion regarding the relationships between the functionality of the precursors, the functionality of the prepolymer, and the preparation of the modified prepolymer is in order.

As already noted, the PICRF should be at least two. When the PICRF is two, crosslinking during the foam-forming reaction can be achieved by using either a polyisocyanate having at least three isocyanate groups per molecule or a mixture of a diisocyanate and one or more polyisocyanates having at least three isocyanate groups per molecule. When the PICRF is three or more, crosslinking can be controlled by increasing the amount of first compound(s) having but one isocyanate-reactive group and/or by adding one or more other compounds having but one isocyanate-reactive group.

Usually, and preferably, the PICRF will be between two and three. This is achieved, as is well known in the art, by employing a mixture of two or more precursors, one of which has a PICRF of two and one of which has a PICRF of three or more. The ratio of the amounts of precursors present and the PICRF values of each determine the average PICRF value for the mixture.

It should be noted, however, that crosslinking still can be achieved when the PICRF is less than two by preparing the prepolymer with an isocyanate having three or more isocyanate groups per molecule. Such a procedure will yield a prepolymer having a prepolymer isocyanate functionality (or PPICF) greater than two. However, a PICRF of less than two requires the presence of precursor molecules having but one isocyanate-reactive group. Such molecules are chain terminating and, as a consequence, can have deleterious effects on polyurethane properties. Such effects may be sufficiently minor when the precursor molecular weight is relatively high. Accordingly, the present invention is deemed to include the use of precursors having a PICRF of less than two, provided that acceptable superabsorbent polyurethane foams can be prepared therewith.

The prepolymer isocyanate functionality (or PPICF) clearly is affected by the PICRF. If a diisocyanate is used to prepare the prepolymer, the PPICF and the PICRF will be the same. However, the PPICF can be either lower or higher than the PICRF by using an appropriate mixture of isocyanates. For example, the use of a mixture of a monoisocyanate and a diisocyanate will reduce the PPICF relative to the PICRF, the extent of such reduction being a function of the amount of monoisocyanate present. Alternatively, a mixture of a diisocyanate and a triisocyanate (or any polyisocyanate having at least three isocyanate groups per molecule) will increase the PPICF relative to the PICRF, the extent of such increase being a function of the amount of triisocyanate (or polyisocyanate) present.

As already indicated, the PPICF must be greater than two. Preferably, the PPICF will be equal to or greater than about 2.3. In addition, the PPICF and the amount of first compound(s) should be adjusted so that the modified prepolymer has an isocyanate functionality greater than two in order for crosslinking to occur during foam formation.

Crosslinking during the foam-forming reaction also can be accomplished by carrying out an addition polymerization reaction between the modified prepolymer and at least one third compound containing at least two carbon-carbon double bonds capable of both homopolymerization and copolymerization with other third compound molecules, and copolymerization with the first compound present in the modified prepolymer. While the nature of such monomers is not known to be critical, especially useful third compounds include the diacrylate and dimethacrylate esters of aliphatic diols, such as the dimethacrylate ester of 1,4-butanediol.

While the superabsorbent polyurethane foams of the present invention perhaps are more easily described in terms of the process for making them, the polycarbonyl moieties are comprised of carbonyl-containing repeating units and can be represented generally by the following formulas:

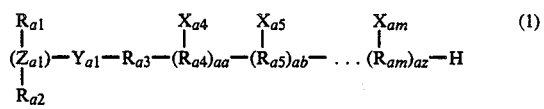

in which $R_{a1}$ represents either hydrogen or $Z_{a2}$; $R_{a2}$ represents either hydrogen or $Z_{a3}$; $R_{a3}$ represents an independent divalent hydrocarbon group which may be substituted or unsubstituted; each of $R_{a4}$, $R_{a5}$, ... and $R_{am}$ independently represents a divalent hydrocarbon group which may be substituted or unsubstituted; $Z_{a1}$, $Z_{a2}$, and $Z_{a3}$ represent portions of the polyurethane; $Y_{a1}$ represents a urethane, thiourethane, or urea linkage; each of $X_{a4}$, $X_{a5}$, ... and $X_{am}$ independently represents carbamoyl, substituted carbamoyl, or carboxy or an alkali metal or ammonium salt thereof; am is an integer which represents the number of different repeating units; and each of aa, ab, ... and az independently represents an integer of from 0 to about 100, with the proviso that the sum of aa, ab, ... and az is in the range of from about 5 to about 100; and

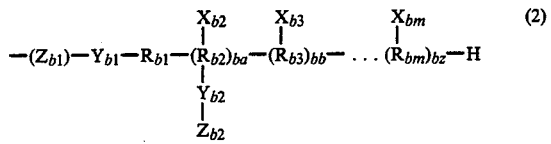

in which $R_{b1}$ represents an independent divalent hydrocarbon group which may be substituted or unsubstituted; each of $R_{b2}$, $R_{b3}$, ... $R_{bm}$ independently represents a divalent hydrocarbon group which may be substituted or unsubstituted; $Z_{b1}$ and $Z_{b2}$ represent portions of the polyurethane; $Y_{b1}$ and $Y_{b2}$ independently represent a urethane, thiourethane, or urea linkage; each of $X_{b2}$, $X_{b3}$, ... and $X_{bm}$ independently represents carbamoyl, substituted carbamoyl, or carboxy or an alkali metal or ammonium salt thereof; bm is an integer which represents the number of different repeating units; and each of ba, bb, ... and bz independently represents an integer of from 0 to about 100, with the proviso that the sum of ba, bb, ... and bz is in the range of from about 5 to about 100.

Although not shown, the repeating units can include other addition polymerizable compounds which do not contain any of the functional groups specified herein for imparting superabsorbency to the foam. The incorporation of such other compounds is not preferred, but is deemed to come within the spirit and scope of the present invention; for simplicity, however, the presence of such other compounds is not specifically provided for by the formulas. In addition, the formulas are somewhat idealized in that purely block copolymers rarely will be realized under the conditions of the addition polymerization reaction. Thus, the formulas are used herein with the understanding that random copolymers are covered thereby; indeed, it is intended that such formulas cover any polycarbonyl moiety which is prepared by the addition polymerization of any combination of second compounds.

For preferred embodiments, formula (I) can be rewritten as follows:

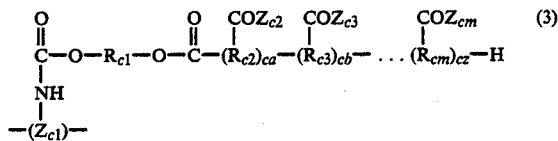

in which $Z_{c1}$ represents a portion of the polyurethane; $R_{c1}$ is an independent divalent hydrocarbon group which may be either substituted or unsubstituted; each of $R_{c2}$, $R_{c3}$, ... and $R_{cm}$ independently represents a divalent hydrocarbon group which may be either substituted or unsubstituted; each of $Z_{c2}$, $Z_{c3}$, ... and $Z_{cm}$ independently represents amino, substituted amino, or $-OM_{c1}$, $-OM_{c2}$, ... and $OM_{cm}$, respectively; each of $M_{c1}$, $M_{c2}$, ... and $M_{cm}$ independently represents hydrogen, an alkali metal, or an ammonium ion; and each of ca, cb, ... and cz independently is an integer of from 0 to about 100, with the proviso that the sum of ca, cb, ... and cz is in the range of from about 5 to about 100.

It is now convenient to turn again to the method of the present invention in order to more fully define the reactants giving rise to the superabsorbent polyurethane foams described and claimed herein.

In general terms, the modified prepolymer is prepared by adding to the prepolymer a first compound having at least one isocyanate-reactive group and at least one carbon-carbon double bond which is capable of undergoing addition polymerization with the second compound under the conditions of the polyurethane foam formation. If the first compound has but a single isocyanate-reactive group, the final polyurethane foam will have polycarboyl moieties represented by formula (1), supra. If the first compound has two isocyanate-reactive groups, the final polyurethane foam will have polycarboyl moieties represented by formula (2). However, the presence of a first compound having three or more isocyanate-reactive groups will result in crosslinking of the modified prepolymer. Such crosslinking, while permissible, is not preferred since it can increase the viscosity of the modified prepolymer, even though the viscosity increase can be partially or wholly corrected for by the use of a solvent. Thus, the preferred first compounds are those having either one or two isocyanate-reactive groups per molecule.

Apart from the requirements for the first compounds already stated, the nature of the first compound is not otherwise known to be critical. Examples of suitable types of first compounds include, among others, unsaturated primary aliphatic amines, unsaturated secondary aliphatic amines, primary aromatic amines having an unsaturated aliphatic substituent, secondary aliphatic amines having an unsaturated aliphatic substituent, unsaturated aliphatic hydrazines, unsaturated amides in which the unsaturation is associated with an aliphatic moiety, unsaturated aliphatic ureas, unsaturated aliphatic urethanes, unsaturated aliphatic imides, unsaturated aliphatic amidines, unsaturated aliphatic nitramines, unsaturated aliphatic diazoamino compounds, phenylhydrazones having an unsaturated aliphatic substituent, unsaturated aliphatic aminooximes, unsaturated aliphatic sulfimides, acylureas having an unsaturated aliphatic substituent, unsaturated aliphatic thioureas, unsaturated aliphatic isothioureas, unsaturated primary alcohols, unsaturated secondary alcohols, phenols having an unsaturated aliphatic substituent, unsaturated aliphatic carboxylic acids, aromatic carboxylic acids having an unsaturated aliphatic substituent, unsaturated malonic esters, nitroalkenes, unsaturated aliphatic acetoacetic esters, unsaturated primary mercaptans, unsaturated secondary mercaptans, thiophenols having an unsaturated aliphatic substituent, and the like.

Examples of suitable first compounds include, by way of illustration only, ethylene glycol; monoallyl ether; aminoethylene; acrylic acid; methacrylic acid; hydroxyethyl acrylate; hydroxymethyl methacrylate; 3-hydroxypropyl acrylate; 2-hydroxypropyl methacrylate; aminoethyl acrylate; 3-mercaptobutyl methacrylate; 1-phenyl-2-propene-2-ol; 2-butene-1,4-diol; 2-butenoic acid;

allyl 2-butenoate; ethyl 3-amino-2-butenoate; 4-chloro-2-butenoic acid; 3-butenoic acid; ethyl 2-hydroxy-3-butenoate; 2-butene-1-ol; 4-chloro-2-butene-1-ol, 3-butene-1-ol; 2-chloro-3-butene-1-ol; 4-(2-hydroxyphenyl)-3-butene-2-one; isobutylene glycol; 3-chloroisobutylene glycol; allyl alcohol; 2-chloroallyl alcohol; 2-bromoallyl alcohol; 3-(4-hydroxyphenyl)allyl alcohol; allylamine; N-methylallylamine; N-phenylallylamine; allyl mercaptan; acetaldehyde phenylhydrazone; allyl acetoacetate; 3,4-dihydroxy-1-allyl-benzene; 5-allyl-2-hydroxy-3-methoxybenzoic acid (eugenic acid); 4-allyl-2-methoxyphenol; 1,2-butadiene-4-ol; 1-butene-3,4-diol; 2-butene-1,4-diol; cinnamamide; cinnamic acid; 2-aminocinnamic acid; 4-carboxycinnamic acid; 2,4-dihydroxycinnamic acid (umbellic acid); 3-hydroxycinnamic acid; cinnamyl alcohol; crotonamide; 1-cyclohexenylcyanoacetic acid; cyclohexene-1-carboxylic acid; 2-cyclohexene-1-ol; 5-methyl-2-cyclohexene-1-ol; 3-cyclohexene-1-ol; diallylamine; fumaric acid; chlorofumaric acid; mesaconic acid; 2-methyl-6-methylamino-2-heptene; 2-heptene-1-ol; 1,5-hexadiene-3,4-diol; 2,4-hexadienedioc acid; 2,4-hexadiene-1-ol; 3-hexenoic acid; 3-hexene-1-ol; 1,2-diallylhydrazine; allylhydrazine; itaconic acid; linoleic acid; maleic acid; allylmalonic acid; methallyl alcohol; methacryl amide; 4-methyl-2-pentenoic acid; allylacetic acid; 1-pentene-3-ol; 2-allylphenol; 4-allylthiophenol; 2-allyl-4-chlorophenol; 2-allyl-4-bromothiophenol; 2-allyl-6-methoxyphenol; 2-vinylphenol; 3-vinylthiophenol; 2-allylpiperidine; propenoic acid; 1-phenyl-2-propene-1-ol; 2,2'-diaminostilbene; 4,4'-dihydroxystilbene; 2-aminostyrene; 3-aminostyrene; 4-aminostyrene; 2-hydroxystyrene; 3-hydroxystyrene; 4-hydroxystyrene; 3-mercaptostyrene; 1-allylthiourea; 2-allyltoluene; 2-isopropyltoluene; and the like.

The most preferred first compounds are hydroxy-containing esters of acrylic acid and methacrylic acid, such as hydroxyethyl acrylate and hydroxyethyl methacrylate, especially when the second compounds are acrylate and methacrylate salts. More generally, the preferred first compounds are hydroxy- or amino-containing aliphatic compounds having no more than about six carbon atoms, with hydrocarbons, esters, and ethers being more preferred.

The amount of first compound employed will be selected in order to maintain an isocyanate functionality of the modified prepolymer greater than two. As already explained, such amount must be chosen in conjunction with the PPICF and the amount of second compound. In addition, the weight of first compound added also will be dependent upon the molecular weight of such compound. Consequently, it is not possible to specify a range for the amounts of first compound which can be used. As a practical matter, however, the amount of first compound often will be in the range of from about 1 to about 5 percent by weight, based on the amount of prepolymer employed.

When the first compound is a liquid, a solvent often is not required since the prepolymer usually is a liquid as well. A solvent may be necessary, however, if the first compound is a solid or if the viscosity of the resulting reaction mixture is too high to allow complete mixing.

In general, any solvent can be used which is not reactive with any of the components of the reaction mixture and in which the reactants are sufficiently soluble. Examples of suitable solvents include, by way of illustration only, aliphatic ketones, such as acetone, methyl ethyl ketone, methyl propyl ketone, and the like; aliphatic esters of the lower aliphatic carboxylic acids, such as ethyl acetate, methyl propionate, butyl acetate, and the like; aliphatic esters, such as diethyl ether, methyl propyl ether, and the like; aromatic hydrocarbons, such as benzene, toluene, the xylenes, and the like; halogenated aliphatic hydrocarbons, such as methylene chloride and the like; dioxane; tetrahydrofuran; dimethylformamide; and the like. The amount of solvent used is not known to be critical.

Reaction conditions for the preparation of the modified prepolymer, such as the reaction time and temperature, are not critical, as long as the conditions are selected to allow substantially complete reaction. In general, reaction times will be in the range of from about 1 to about 6 hours, although longer or shorter times can be used. Reaction temperatures typically can vary from ambient temperature to about 100° C., although higher or lower temperatures often are possible, depending upon the reaction mixture viscosity, the presence or absence of a solvent, and the reactivities of the reaction mixture components. As a rule, higher reaction temperatures usually permit shorter reaction times.

As will be apparent to those having ordinary skill in the art, the reaction leading to the modified prepolymer should be conducted in the absence of water. However, extraordinary measures need not be taken. It is necessary, though, to ensure that all reactants and solvents, if employed, are dry.

Normally, the modified prepolymer thus obtained does not require purification or other processing before carrying out the foaming reaction. If a solvent has been used, it may be desirable to remove it, usually under reduced pressure, in order to avoid the presence of solvent in the superabsorbent polyurethane foam. It is not imperative that solvent be removed, however, especially if a relatively small amount of a relatively volatile solvent has been employed. Preferably, a substantial amount of solvent will not be present in the modified prepolymer.

Once prepared, the modified prepolymer then is reacted with an aqueous solution of second compound in the presence of a thermally activated free radical initiator. The reaction typically is carried out at ambient temperature, although lower or higher temperatures can be used. The foaming reaction is exothermic. If the free radical initiator is activated at a sufficiently low temperature, the exotherm activates the free radical initiator which in turn causes the free radical polymerization of the second compound with the first compound and with itself. If the exotherm is insufficient to activate the free radical initiator, the foam can be heated at a temperature which will cause activation of the initiator and for a period of time sufficient to allow the addition polymerization to take place. Thus, the addition polymerization can be carried out simultaneously with or subsequent to the polyurethane foam formation reaction.

The second compound in general is selected from the group consisting of carboxylic acid amides in which the amido moiety can be substituted or unsubstituted, and carboxylic acids and alkali metal and ammonium salts thereof, which compounds have at least one carbon-carbon double bond capable of undergoing addition polymerization with the first compound and with itself under the conditions of the foaming reaction.

The second compound can contain more than one functional group as long as there is present in the compound at least one carbamoyl, substituted carbamoyl, or carboxy group or alkali metal or ammonium salt thereof and the additional functional groups do not significantly adversely affect either the polymerization reactions or the properties of the resulting foam. Thus, when two or more functional groups are present in any second compound, such groups can be the same or different. Moreover, all functional groups present in the compound can be selected from the foregoing group of required functionality, if desired. When all of the functional groups are carboxy groups, such groups can be present partly as the free acid and partly as a salt.

By way of illustration only, suitable second compounds include, among others, acrylic acid, methacrylic acid, 2-butenoic acid, 4-chloro-2-butenoic acid, 3-butenoic acid, 5-allyl-3-methoxybenzoic acid, cinnamic acid, 2-carboxycinnamic acid, 4-carboxycinnamic acid, 1-cyclohexenylcyanoacetic acid, cyclohexene-1-carboxylic acid, fumaric acid, chlorofumaric acid, mesaconic acid, 2,4-hexadienedioc acid, 3-hexenoic acid, itaconic acid, linoleic acid, maleic acid, allylmalonic acid, 4-methyl-2-pentenoic acid, allylacetic acid, propenoic acid, the amides thereof, the substituted amides thereof, the alkali metal salts thereof, the ammonium salts thereof, and the like. Among the ammonium salts, those derived from ammonia and the primary lower alkyl amines are preferred, with those derived from ammonia being most preferred. The preferred compounds are acrylic acid, methacrylic acid, and the amides and potassium salts thereof. Acrylamide and the potassium salts of acrylic and methacrylic acid are the most preferred second compounds.

In selecting the second compound, it is preferred that the reactivity of the double bond thereof in addition polymerization reactions be approximately the same as that of the double bond of the first compound. If such reactivity of the double bond of the second compound is significantly greater than that of the double bond of the first compound, there is an increased possibility that the second compound preferentially will polymerize with itself (or copolymerize with other second compounds present in the reaction mixture). If this happens, the second compound will form polymers (or copolymers) which are not covalently attached to the polyurethane making up the superabsorbent foam. Such a result is undesirable for applications where relatively permanent superabsorbency is required, i.e., when extraction of the polymers (or copolymers) is to be avoided.

The amount of second compound employed is in part dependent upon the degree of superabsorbency desired and the solubility of the second compound in water. Generally, the amount of second compound present in the aqueous solution will be in the range of from about 5 to about 100 moles per mole of total first compound present in the modified prepolymer. The lower limit is the approximate minimum required to give a superabsorbent polyurethane foam, provided that a sufficient amount of first compound has been incorporated into the modified prepolymer. The upper limit, however, is more a function of second compound solubility than anything else. Thus, if an extremely water-soluble second compound were employed, the upper limit could be greater.

It should be appreciated by those having ordinary skill in the art that the above limits are given by way of suggestion only. Because the degree of superabsorbency achieved with any polyurethane foam primarily is a function of the number and types of carbonyl groups, the number or chain lengths of the polycarbonyl moieties should not be critical. Stated differently, the number of sites for the attachment of the polycarbonyl moieties to the polyurethane is a function of the amount of first compound reacted with the prepolymer to make the modified prepolymer. A reduction in the number of such sites, such as may be required with a prepolymer having a lower PPICF, can be compensated for by increasing the chain lengths of the polycarbonyl moieties. Thus, the degree of superabsorbency normally will not be a function of the amount of first compound present in the modified prepolymer. However, it should be apparent to one having ordinary skill in the art that the amount of first compound present in the modified prepolymer has a direct bearing on the approximate lower limit given above for the amount of second compound present in the aqueous solution.

Preferably, the amount of second compound in the aqueous solution will be in the range of from about 10 to about 50, and most preferably from about 10 to about 40, moles per mole of first compound in the modified prepolymer.

The lower limit of the broad range given above is approximately equivalent to about $0.8 \times 10^{-3}$ mole of second compound in the aqueous solution per g of modified prepolymer. Preferably, such amount will be at least about $1.5 \times 10^{-3}$, and most preferably at least about $2 \times 10^{-3}$, mole per g of modified prepolymer. It must be emphasized, though, that these values are given by way of illustration only, in part because the superabsorbency obtained with any given second compound is affected by the nature of the precursor.

In view of the foregoing discussion, it should be apparent that the amount of second compound on a weight basis can vary widely. By way of illustration only, such amount often will be in the range of from about 20 to about 50 percent by weight, based on the weight of modified prepolymer employed.

As already stated, the initiator is dissolved in either the modified prepolymer or the aqueous solution in which the second compound is dissolved. The choice of phase does not appear to be critical and is primarily a function of initiator solubility. In general, as already noted, the addition polymerization reaction can be carried out during or after the foaming reaction. Preferably, the addition polymerization reaction will be carried out during the foaming reaction.

In general, the free radical initiator can be any of the known initiators for free radical addition polymerization. Examples of such initiators include, by way of illustration only, acyl peroxides, such acetyl peroxide, benzoyl peroxide, bromobenzoyl peroxide, and the like; alkyl peroxides, such as cumyl peroxide, t-butyl peroxide, lauryl peroxide, and the like; hydroperoxides, such as t-butyl hydroperoxide, cumyl hydroperoxide, and the like; peresters, such as t-butyl perbenzoate, t-butyl peracetate, and the like; azo compounds, such as 2,2'-azobisisobutyronitrile, p-bromobenzenediazo hydroxide, triphenylmethylazobenezene, and the like; disulfides; tetrazenes; testraphenylsuccinonitrile; hydrogen peroxide and ferrous ions; potassium peroxysulfate; ammonium peroxysulfate; and the like.

Because satisfactory results have been achieved with the use of 2,2-azobisisobutyronitrile and ammonium peroxysulfate, such compounds are preferred. Ammonium peroxysulfate can be used in the presence of N,N,N',N'-tetramethylethylene diamine which causes a lowering of the activation temperature of the ammonium peroxysulfate to a temperature within the range of the exotherm produced by the foaming reaction. The combination of ammonium peroxysulfate with N,N,N',N'-tetramethylethylene diamine is most preferred since it results in simultaneous foaming and addition polymerization reactions. Of course, other low temperature activated initiators can be used.

If desired, more than one free radical initiator can be employed. For example, one initiator could have a relatively low activation temperature and a second initiator could have a higher activation temperature. The first initiator would be activated early in the foaming process, whereas the second initiator would be activated later, such as during a post-foaming polymerization step.

The amount of initiator employed is not known to be critical, provided that the amount is sufficient to initiate the addition polymerization. Typically, the amount of initiator will be in the range of from about 0.5 to about 5 percent by weight, based on the amount of second compound present in the aqueous solution. Preferably, the amount of initiator will be in the range of from about 1 to about 3 percent by weight.

Other methods for preparing the compositions of the present invention can be employed, if desired, such as the so-called "one-shot" process and the "semi-prepolymer" process. For a general discussion of methods for preparing polyurethane foams, see, e.g., Saunders and Frisch, supra, pp. 223–227.

The present invention is further illustrated by the examples which follow. Such examples, however, are not to be construed as in any way limiting the spirit and scope of the present invention. In the examples, all temperatures are in degrees Celsius, unless specified otherwise.

EXAMPLE 1

Preparation of Modified Prepolymer

A 1-l, four-necked, round-bottomed reaction flask fitted with a stirrer, thermometer, nitrogen inlet tube, and calcium chloride drying tube was charged with 693.6 g of a toluene diisocyanate-terminated poly(oxyethylene) polyol having a molecular weight of 1,400, a PPICF of 2.3, and a free toluene diisocyanate content of 0.3 percent by weight (HYPOL ® FHP 2002, W. R. Grace & Co., Organic Chemicals Division, Lexington, Mass.), and 12.89 g of 2-hydroxyethyl methacrylate (Eastman Kodak Company, Rochester, N.Y.). The flask was flushed with dry nitrogen. The mixture was stirred slowly and heated to 30°. The flask then was charged with 0.35 g of triethylamine. The resulting mixture was stirred and heated to 50° and maintained at that temperature for three hours while keeping a dry nitrogen atmosphere in the flask. The reaction mixture then was allowed to cool to ambient temperature. The resulting modified prepolymer had an isocyanate functionality of 2.1.

EXAMPLE 2

Preparation of Superabsorbent Polyurethane Foam

A 1-qt. (0.95 l) stainless steel mixing cup was charged with 150 g of the modified prepolymer of Example 1, to which was added 1.1 g of 2,2'-azobisisobutyronitrile dissolved in 4.5 g of dry acetone. The resulting mixing was stirred slowly until homogeneous. To the mixing cup was added 150 g of a potassium methacrylate solution prepared by diluting 100 g of 37 percent by weight aqueous potassium methacrylate with 50 g of deionized water. The contents of the mixing cup were mixed immediately for about 5 sec under high shear using a Hamilton Beach Model 936 Drink Mixer (Scovil, Inc., Hamilton Beach Division, Waterbury, Conn.). The resultant foaming mixture was poured into a Teflon-coated pan which had been lightly coated with a partially hydrogenated vegetable oil/alcohol/lecithin aerosol (PAM TM, Boyle-Midway, Inc., New York, N.Y.). The foam was allowed to stand for 5 min at ambient temperature and then was heated in an oven at 110° under an inert atmosphere for one hour. The foam was removed from the oven, allowed to cool, and placed in a polyethylene bag.

A control foam was prepared by repeating the above procedure, except that the 2-hydroxyethyl methacrylate, potassium methacrylate, and free radical initiator were omitted; the amount of water employed to generate the foam was 150 g.

A Saline Retention Value/100 (SRV/100) was determined for the foam of Example 2 and the control foam. Such SRVs/100 were 2.55±0.16 and 0.97±0.03, respectively. The SRV/100 was determined as described in ASTM Test Method D 2402, Standard Test Method for Water Retention of Fibers (Centrifuge Method), except that 0.9 percent by weight aqueous sodium chloride was used in place of water. The foam of Example 2 also exhibited remarkable swelling behavior in the presence of water and a gel-like state when fully hydrated. The foam also demonstrated an enhanced wicking rate relative to the control foam.

EXAMPLE 3

Preparation of Superabsorbent Polyurethane Foam

A 1-qt. (0.95 l) stainless steel mixing cup was charged with 150 g of the modified prepolymer of Example 1. An initiator and third compound solution, prepared by sequentially dissolving 1.1 g of 2,2'-azobisisobutyronitrile and 3.69g of 1,4-butanediol dimethacrylate in 4.4 g of dry acetone, was added to the modified prepolymer. The mixture was stirred slowly until homogeneous. To the mixture then was added a potassium methacrylate solution prepared by diluting 100 g of 37 percent by weight aqueous potassium methacrylate with 46.3 g of deionized water. The contents of the mixing cup were mixed immediately under high shear for about 5 sec and the resulting foam was molded and heated, all as described in Example 2. The SRV/100 of the foam was 2.33±0.14. In appearance, feel, and wicking rate, the foam was similar to that obtained in Example 2.

EXAMPLE 4

Preparation of Modified Prepolymer

The procedure of Example 1 was repeated, except that the amounts of prepolymer, 2-hydroxyethyl methacrylate, and triethylamine were 686.3, 12.76, and 0.34 g, respectively.

EXAMPLE 5

Preparation of Superabsorbent Polyurethane Foam

To a 1-qt. (0.95 l) stainless steel mixing cup was added 150 g of the modified prepolymer of Example 4. A solution of 50 g of acrylamide and 0.4 g of ammonium peroxysulfate in 100 g of deionized water was added to the modified prepolymer, followed by the immediate addition of 0.5 ml of N,N,N',N'-tetramethylethylene diamine. The resulting mixture was stirred for 2 sec as described in Example 2. The foaming reaction mixture was poured into a pan as described in Example 2 and covered. An exotherm and steam generation were observed in the foam. The foam was allowed to stand for about 15 min and then was placed in a polyethylene bag. The resulting foam was harder and stiffer than those obtained in Examples 2 and 3. Upon exposure to water, however, the foam became swollen, soft, flexible, and gel-like. The SRV/100 of the foam was 1.57±0.02. The foam did not exhibit the enhanced wicking rates observed with the foams of Examples 2 and 3.

EXAMPLE 6

Preparation of Superabsorbent Polyurethane Foam

The procedure of Example 5 was repeated, except that the acrylamide solution consisted of 47 g of acrylamide, 3.0 g of N,N'-methylenebisacrylamide, and 0.4 g of ammonium peroxysulfate in 100 g of deionized water. The resulting foam had an SRV/100 of 1.35±0.02 and resembled the foam of Example 5.

EXAMPLE 7

Preparation of Modified Prepolymer

A 1-l, four-necked, round-bottomed reaction flask fitted with a stirrer, thermometer, gas inlet tube, and a calcium chloride drying tube was charged with 352 g of a poly(oxyalkylene) tetraol having a molecular weight of 500 and a PICRF of four (PLURACOL ® PEP 550, BASF Wyandotte, Parsippany, N.J.) and flushed with dry air. The tetraol was stirred and heated to 150° for 30 min to drive off residual moisture. Upon cooling to ambient temperature, the flask was charged with 147.5 g of 2-hydroxyethyl acrylate (Eastman Kodak Company, Rochester, N.Y.) which had been stored over a molecular sieve (Fisher 3 Å Grade 564, W. R. Grace & Co., Davison Division, Baltimore, Md.) which had been washed with methanol and dried overnight in an oven at 130° under reduced pressure (about 252 mm Hg). The contents of the flask were stirred slowly to obtain a homogeneous mixture. The flask then was charged with 492.0 g of an 80-20 mixture of 2,4-and 2,6-toluenediisocyanate. Upon stirring the contents of the flask, heat was evolved, the mixture turned from clear to amber, and the mixture viscosity increased with time. The mixture was maintained at about 50° for 3 hrs and then at about 60° for about 1 hr. The reaction mixture then was allowed to cool to ambient temperature.

EXAMPLE 8

Preparation of Superabsorbent Polyurethane Foam

A Waring Blender was charged with 150 g of the modified prepolymer of Example 7. To the Blender were added in rapid succession a solution of 0.45 g of ammonium peroxysulfate in 5.0 g of deionized water, 200 g of 55 percent by weight aqueous potassium acrylate, and 0.5 ml of N,N,N',N'-tetramethylethylene diamine. The Blender contents were blended under high shear for several seconds and the resulting foaming mixture was poured into a glass pan coated with mineral oil. Heat and steam were evolved by the foam upon standing. The foam was rigid and somewhat brittle, with an SRV/100 of 5.03±0.25.

Upon repeating the procedure of Example 8, similar results were obtained, except that the foam had an SRV/100 of 3.91±0.11.

EXAMPLE 9

Preparation of Superabsorbent Polyurethane Foam

The procedure of Example 8 was repeated, except that the amount of potassium acrylate solution was increased to 250 g. The foam obtained was similar to that of Example 8 and had an SRV/100 of 4.28±0.13.

EXAMPLE 10

Preparation of Superabsorbent Polyurethane Foam

The procedure of Example 8 was repeated, except that the amount of modified prepolymer was reduced to 100 g and the amount of potassium acrylate solution was increased to 250 g. The resulting foam was similar to that of Example 8 and had an SRV/100 of 5.74±0.25.

Having thus described the invention, numerous changes and modifications thereto will be apparent to those having ordinary skill in the art without departing from the spirit and scope of the present invention.

What is claimed is:

1. A method of preparing a superabsorbent cross-linked polyurethane foam which comprises the steps of:
    A. mixing an isocyanate-terminated polyurethane prepolymer having an isocyanate functionality greater than two with at least one first compound having at least one isocyanate-reactive group and at least one carbon-carbon double bond, the amount of said first compound being insufficient to reduce the isocyanate functionality of the prepolymer to a value equal to or less than two;
    B. allowing the mixtue obtained in Step A to substantially completely react; and
    C. mixing the reaction product from Step B with an aqueous solution of at least one carbonyl-containing second compound having at least one carbon-carbon double bond capable of undergoing addition polymerization with said first compound and with itself under the conditions of the polyurethane foam formation, the carbonyl group of said second compound being selected from the group consisting of carbamoyl, substituted carbamoyl, and carboxy and the alkali metal and ammonium salts thereof;
    in which at least one thermally activated free radical initiator has been dissolved in either the reaction product from Step B or said aqueous solution, said carbon-carbon double bond of said first compound is capable of undergoing addition polymerization with said second compound under the conditions of the polyurethane foam formation; and the proportions of said first and second compounds are selected to impart superabsorbent properties to the resulting polyurethane foam.

2. The method of claim 1, in which said isocyanate functionality is equal to or greater than about 2.3.

3. The method of claim 1, in which said first compound is selected from the group consisting of hydroxyethyl acrylate and hydroxyethyl methacrylate.

4. The method of claim 1, in which said second compound is selected from the group consisting of acrylamide, potassium acrylate, and potassium methacrylate.

5. The method of claim 1, in which, prior to carrying out Step C, the reaction product from Step B is mixed with (1 ) at least one third compound having at least two carbon-carbon double bonds capable of both homopolymerization and copolymerization with other third compound molecules, and copolymerization with first compound present in said reaction product, and (2) a free radical initiator if not already present, and the resulting mixture is subjected to conditions sufficient to assure addition polymerization of the unsaturated components thereof.

6. The method of claim 5, in which the at least one third compound is selected from the group consisting of the diacrylate and dimethacrylate esters of aliphatic diols.

7. The method of claim 6, in which the at least one third compound is the dimethacrylate ester of 1,4-butanediol.

* * * * *